(12) United States Patent
Mann et al.

(10) Patent No.: US 6,266,568 B1
(45) Date of Patent: Jul. 24, 2001

(54) INFLATABLE COCHLEAR ELECTRODE ARRAY AND METHOD OF MAKING SAME

(75) Inventors: Alfred E. Mann, Beverly Hills, CA (US); Thomas H. R. Lenarz, Hannover (DE); Janusz A. Kuzma, Englewood, CO (US); William Vanbrooks Harrison, Valencia, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/300,800

(22) Filed: Apr. 27, 1999

Related U.S. Application Data (63) Continuation-in-part of application No. 09/247,734, filed on Feb. 9, 1999, now Pat. No. 6,129,753, and a continuation-in-part of application No. 09/140,033, filed on Aug. 26, 1998, now Pat. No. 6,070,105.
(60) Provisional application No. 60/087,653, filed on Jun. 2, 1998.

(51) Int. Cl.[7] .................................................. A61N 1/04
(52) U.S. Cl. ........................................................ 607/137
(58) Field of Search ................................... 607/136, 137, 607/122

(56) References Cited

U.S. PATENT DOCUMENTS

| | | | |
|---|---|---|---|
| 4,819,647 | 4/1989 | Byers et al. ........................ | 128/642 |
| 4,832,051 | 5/1989 | Jarvik et al. ....................... | 128/784 |
| 4,898,183 | 2/1990 | Kuzma ................................ | 128/784 |
| 4,991,582 | 2/1991 | Byers et al. ........................ | 128/419 |
| 5,000,194 | 3/1991 | van den Honert et al. ......... | 128/784 |
| 5,037,497 | 8/1991 | Stypulkowski ..................... | 156/245 |
| 5,255,678 | * 10/1993 | Deslauriers et al. ................ | 607/122 |
| 5,443,493 | 8/1995 | Byers et al. ........................ | 607/137 |
| 5,545,219 | 8/1996 | Kuzma ................................ | 623/10 |
| 5,578,084 | 11/1996 | Kuzma et al. ...................... | 623/10 |
| 5,603,726 | 2/1997 | Schulman et al. .................. | 607/57 |
| 5,645,585 | 7/1997 | Kuzma ................................ | 623/10 |
| 5,649,970 | 7/1997 | Loeb et al. .......................... | 607/57 |
| 5,653,742 | 8/1997 | Parker et al. ....................... | 607/137 |
| 5,667,514 | 9/1997 | Heller ................................. | 606/108 |
| 6,074,422 | * 6/2000 | Berrang et al. .................... | 607/137 |

FOREIGN PATENT DOCUMENTS 9631087  3/1996 (WO).

\* cited by examiner

*Primary Examiner*—Scott M. Getzow
(74) *Attorney, Agent, or Firm*—Bryant R. Gold (57) ABSTRACT

An inflatable cochlear electrode array adapted for insertion into a human cochlear includes a flexible carrier on which a multiplicity of spaced-apart electrode contacts are carried, preferably along one side, e.g., a medial side, of the carrier. The flexible carrier also includes an inflatable compartment or section. In one embodiment, the inflatable section is located at the distal tip of the electrode array on a side of the flexible carrier that is opposite the electrode contacts. In another embodiment, the inflatable compartment or section is located along at least one half of the full length of the flexible carrier, forming a spine. In either embodiment, the electrode is readily inserted into the cochlea to a desired depth while the inflatable compartment or section remains in a deflated state. Thereafter, a desired modiolus-hugging position is achieved by inflating the inflatable compartment or section by injecting therein a suitable biocompatible fluid. A method of making an inflatable cochlear electrode is also disclosed.

16 Claims, 9 Drawing Sheets

INFLATABLE COCHLEAR ELECTRODE ARRAY AND METHOD OF MAKING SAME

This application is a continuation-in-part of application Ser. No. 09/140,033, filed Aug. 26, 1998 now U.S. Pat. No. 6,070,105; and Ser. No. 09/247,734, filed Feb. 9, 1999 now U.S. Pat. No. 6,129,753. Further, this application claims the benefit of U.S. Provisional Patent Application Ser. No. 60/087,653, filed Jun. 2, 1998, which patents and application are incorporated herein by reference.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers. More particularly, the invention relates to an electrode array having an inflatable portion that may be inserted into the cochlea while the inflated portion is deflated. After insertion, the inflated portion may be inflated, thereby positioning the electrode contacts near or against the modiolus.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of separating the acoustic signal into a number of parallel channels of information, each representing the intensity of a narrow band of frequencies within the acoustic spectrum. Ideally, each channel of information should be conveyed selectively to a subset of auditory nerve cells that normally transmits information about that frequency band to the brain. Those nerve cells are arranged in an orderly tonotopic sequence, from high frequencies at the basal end of the cochlear spiral to progressively lower frequencies towards the apex.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is typically pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647, incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it is generally believed that enhanced performance of a cochlear implant may be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned farther away from the modiolar wall than they should be for optimum performance.

It is thus seen that there are few cochlear electrode designs that allow placement of the electrode contacts in close proximity to the modiolar wall and the spiral ganglion cells.

Applicant Kuzma has several prior patent applications that disclose various approaches for making and inserting a modiolus-hugging electrode system that address the above problems, including the parent applications of this application, i.e., U.S. patent applications Ser. No. 09/140,033, filed Aug. 26, 1998 (now U.S. Pat. No. 6,070,105); and Ser. No. 09/247,734, filed Feb. 9, 1999 (now U.S. Pat. No. 6,129,753). Reference is also made to the additional U.S. patent applications: Ser. No. 09/140,035, filed Aug. 26, 1998 (now U.S. Pat. No. 6,125,302); and Ser. No. 09/140,034, filed Aug. 26, 1998 (now U.S. Pat. No. 6,038,484), each of which is incorporated herein by reference.

The present application represents yet another approach for achieving the overall goal of placing the electrode contacts in close proximity to the modiolar wall and the spiral ganglion cells.

SUMMARY OF THE INVENTION

The present invention addresses the above and other needs by providing an electrode array designed to assure that the electrode contacts assume a close hugging relationship with the modiolus once implantation of the electrode has occurred. More particularly, the present invention discloses various embodiments of an electrode equipped with an inflatable portion, which allows for easy insertion of the electrode while in a deflated state, and modiolus-hugging positioning after insertion while in an inflated state.

In a first embodiment, the present invention provides an electrode array having an inflatable tip. In a second embodiment, the invention provides an electrode array having an inflatable wall along its back side, thereby forming an inflatable spine.

The electrode array configuration used with both embodiments may assume various forms, as is known in the art. For example, a preferred electrode array is a universal electrode of the type disclosed in the above referenced Ser. No. 09/140,034 patent application; or as further disclosed in Applicant Kuzma's subsequent application, entitled "Cochlear Electrode Array with Electrode Contacts On Medial Side", Ser. No. 09/247,734, filed Feb. 9, 1999 now U.S. Pat. No. 6,129,753.

In the first embodiment, the electrode array is equipped with a thin-wall balloon connected to a small channel within the silicone body carrier of the electrode array. During insertion, the balloon remains deflated, allowing easy insertion to the desired depth. Once the electrode in is place, the balloon is inflated through the channel with a biocompatible liquid, e.g., saline solution. As a result of the inflation, the tip of the electrode is pushed toward the modiolus and wedged into the scala tympani channel, thereby positioning the electrode contacts at the tip of the electrode closer to the modiolar wall and the spiral ganglion cells. The injection of the fluid may be done through a tube which forms an extension of the small channel connected to the balloon. After the balloon is inflated, this tube may be closed by any suitable closing or sealing means, e.g., by crimping a metal band around the tube, to prevent escape of the liquid.

In order to position the remaining electrodes in close proximity to the modiolar wall, the electrode is pulled back about 7 mm after the tip has been inflated and sealed. The tip of the electrode, fixed or anchored by the balloon, remains in place while the rest of the array wraps snugly around the modiolus. Then, at the basal end of the cochlea, the cocli-leostomy is packed with tissue or a special plug in order to fix the electrode at the basal end, thereby maintaining the tight wrap of the electrode snugly around the modiolus.

In the second embodiment, the electrode array is configured to have a thin-wall inflatable section along its full length, forming an inflatable spine portion. This inflatable spine portion or section is in fluid communication with an extended injection/inflation tube and associated sealing or closing ring, or other sealing means. The electrode is inserted into the scala tympani while the inflatable spine portion is in a deflated state. Once inserted to the desired depth, the inflatable spine portion is inflated by injecting a suitable fluid, e.g., saline solution, through the inflation tube. Such inflation causes the inflatable electrode to inflate and fill the entire space of the scala tympani channel, thereby positioning the electrode contacts closer to the modiolus. As it does so, the electrode array typically either moves deeper into the cochlea or it moves slightly backward through the cochleostomy.

The present invention also contemplates a method of making a cochlear electrode array with an inflatable compartment. This is done by making an electrode array having the electrode contacts at a desired spacing and location, e.g., on a medial side, of a flexible carrier, using the techniques disclosed in the referenced patent applications. The method of the present invention may be summarized as involving the following steps: (1) a contact array assembly is made by welding spaced-apart electrode contacts and wire leads to an iron foil carrier; (2) a thin silicone tube (which will function as the inflation tube) is placed on top of this assembly; (3) a top mold, pressed from an iron foil (of the same type used to hold the contact array and leads), and having at least one vent hole therein, is placed over the contact array/silicone tube assembly and the side edges of the respective iron foils, i.e., the foil of the contact array/silicone tube assembly and the foil of the top mold, are sealed together, thereby forming an iron die wherein the top mold is held in a fixed relationship relative to the bottom assembly; (4) liquid silicone elastomer is injected into the iron die to fill all cavities; (5) air (or another suitable gas) is blown through the inflation tube as the liquid silicone elastomer cures, resulting in part of the silicone being pushed out of the die cavity and leaving a layer over the electrode contacts and wire leads as well as a thin film on the surface of the top mold, forming the inflatable section (i.e., balloon wall) of the array; and (6) the entire iron die is chemically etched away, leaving behind the electrode array with a very thin-wall expandable section.

Advantageously, the inflatable electrode array of the present invention achieves the following goals: (1) it virtually guarantees that the electrode array will be optimally positioned against the modiolar wall in a cochlea of any size; (2) the insertion of the electrode array avoids or produces minimal trauma to the cochlear structure; (3) it can be manufactured using easy, low cost technology; and (4) the electrode can be easily removed and reinserted, if required.

BRIEF DESCRIPTION OF THE DRAWINGS

The above and other features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches one type of electrode system that may be used with a cochlear stimulation system. Other electrodes and electrode systems may also be used for this purpose as disclosed, e.g., in the previously-referenced and -filed patent applications, each of which has been incorporated herein by reference. The materials, dimensions, methods of manufacture, and the like, described in these prior-filed patent applications are also applicable to the present invention.

Figure 1:
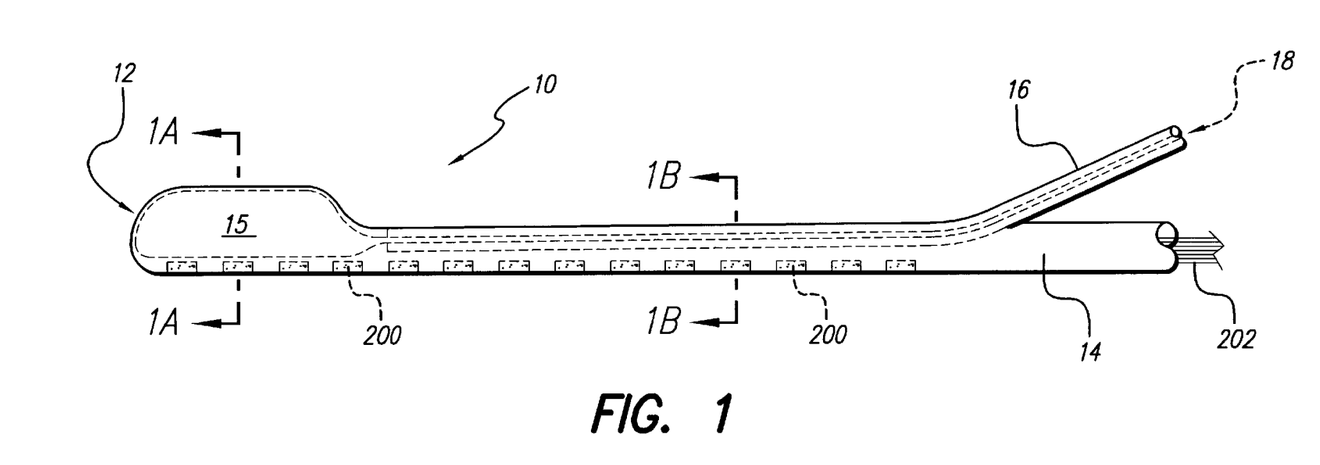
FIG. 1 is a schematic side view of an inflatable electrode array made in accordance with a first embodiment of the present invention.

Turning first FIG. 1, there is shown is a schematic side view of an inflatable electrode array 10 made in accordance with a first embodiment of the present invention. In this first embodiment, the electrode array 10 has an inflatable distal tip 12. In a second embodiment (not shown in FIG. 1, but discussed below in conjunction with FIGS. 6 through 8B), an electrode array 10" has an inflatable wall along its back side, forming an inflatable spine.

The electrode array portion of the inflatable electrode array of the present invention may assume various forms, as is known in the art. That is, an electrode array having exposed ball electrodes spaced-apart along the length of a silastic carrier could be used, as taught, e.g., in U.S. Pat. No. 4,819,647. Alternatively, and preferably, a universal electrode array of the type disclosed in the above referenced Ser. No. 09/140,034 parent patent application now (U.S. Pat. No. 6,038,484); and/or as further disclosed in Applicant Kuzma's subsequent application, entitled "Cochlear Electrode Array with Electrode Contacts On Medial Side", Ser. No. 09/247,734, filed Feb. 9, 1999 (now U.S. Pat. No. 6,129,753), may be used. Such electrode array 10 has a multiplicity of exposed electrode contacts 200, e.g., sixteen electrode contacts 200, spaced apart along one side, e.g., a medial side, of a silastic carrier 14. Each of the electrode contacts is electrically connected to at least one wire 202 that is embedded within the silastic carrier 14. These wires 202 may then be connected to a suitable stimulator device (not shown in FIG. 1) in conventional manner, thereby enabling an electrical stimulus signal to be applied through the electrode contacts 200 to the modiolar wall for the purpose of exciting the spiral ganglion cells.

Preferably, as taught in the referenced patent applications, the electrode contacts are embedded within a slightly pre-curved silastic carrier 14. This construction provides an electrode array 10 that bends easily in a medial direction, but does not bend as easily in directions other than the medial direction. Such construction thus helps assure that the electrode array will not easily twist as it is inserted into the cochlea, thereby helping to assure that the electrode contacts 200 remain facing the modiolar wall of the cochlea as the electrode array 10 is inserted into and winds through the spiraling channel that makes up the scala tympani of the cochlea.

Figure 1A:
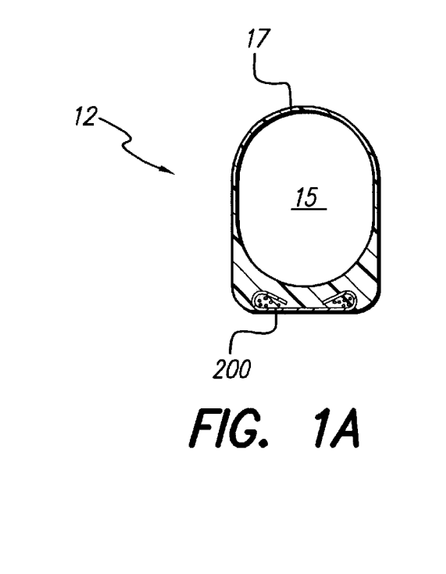
FIG. 1A and FIG. 1B are sectional views of the electrode array shown in FIG. 1 taken along the lines 1A—1A and 1B—1B, respectively.
Figure 1B:
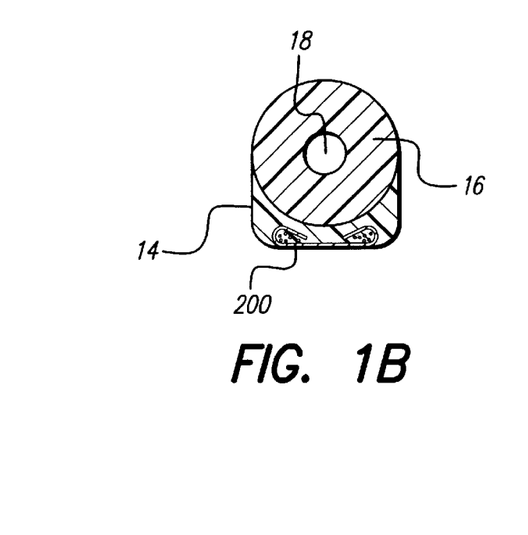

As seen in FIG. 1, as well as the sectional views of FIGS. 1A and 1B, the electrode array 10 is equipped with an inflatable distal tip 12, which functions as a balloon located at the distal tip of the electrode array. This balloon has a thin wall 17 around all but the electrode-contact side thereof. The inside of the thin-walled balloon functions as an inflatable compartment 15. This inflatable compartment 15 is in fluid communication with, i.e., is connected to, a small channel 18 that passes longitudinally through the silicone body carrier 14 (silastic carrier) of the electrode array 10. As will be evident from the description which follows, the channel 18 comprises the lumen of an injection tube 16 that is molded into the silastic carrier 14.

Figure 2:
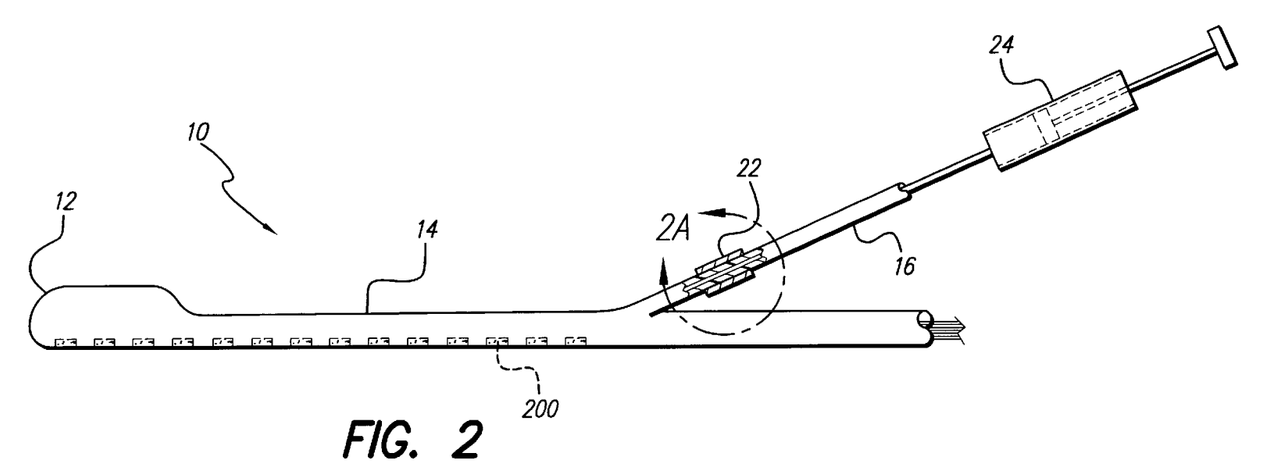
FIG. 2 schematically illustrates inflation of the inflatable compartment of the electrode of FIG. 1.
Figure 2A:
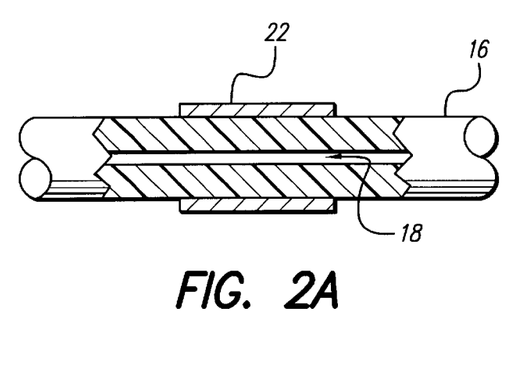
FIG. 2A illustrates the use of a crimp ring placed over the inflation tube in order to seal the tube.
Figure 2B:
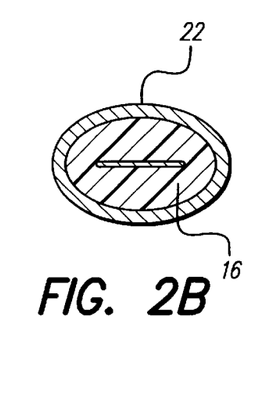
FIG. 2B is a section view of the inflation tube and crimp ring after being crimped or sealed.

When the electrode array 10 is inserted into the cochlea, the balloon 12 (or inflatable tip) remains deflated, allowing easy insertion of the array 10 into the cochlea to the desired depth. Once the electrode array 10 is in place, the balloon 12 is inflated by injecting a biocompatible fluid, e.g., a saline solution, through the channel 18. The injection of the fluid is made possible through the injection tube 16 which is embedded within the silastic carrier 14, and if fact, comprises a significant portion of the silastic carrier 14. As seen in FIG. 1 and FIG. 2, the injection tube 16 extends away from the silastic carrier 14 near a proximal end of the silastic carrier. A sealing means, e.g., a metal band 22, is located around the injection tube near the point where the tube 16 exits from the silastic carrier body 14.

Next, with reference to FIG. 2, the inflation of the inflatable compartment 15 at the distal end of the electrode array 10 is schematically illustrated. The sealing means, e.g., metal band 22, or equivalent closing or crimping member, remains open when the electrode array 10 is initially inserted into the cochlea. That is, the channel 18 remains open when the electrode array 10 is inserted into the cochlea. After insertion to the desired depth, a hypodermic needle 24, or equivalent pumping mechanism, forces a measured volume of biocompatible fluid, e.g., saline solution, through the channel 18 into the balloon cavity 15, thereby inflating the balloon. After inflation of the balloon, the tube 18 is closed, e.g., by crimping the metal band 22, which crimping closes the channel 18, and thereby prevents escape of the fluid. It is to be understood that other types of closing mechanisms may also be used other than a crimping band 22. For example, as is known in the medical implantable catheter art, various silastic membranes exist which may be readily pierced by a sharp needle, but are self-closing, or self-sealing, as soon as the sharp needle is removed. Such a self-sealing membrane may thus be used as a plug at a proximal end of the tube 16, With such a plug, a measured volume of a suitable fluid may thus be readily injected into the balloon compartment 15, thereby inflating the balloon; or removed therefrom, thereby deflating the balloon, using a hypodermic needle 24, or equivalent device. It is also to be understood that fluids other than a saline solution may be used to inflate the inflatable compartment. Any fluid (where "fluid" comprises either liquids and/or gases) that is biocompatible may be used for this purpose.

Figure 3A:
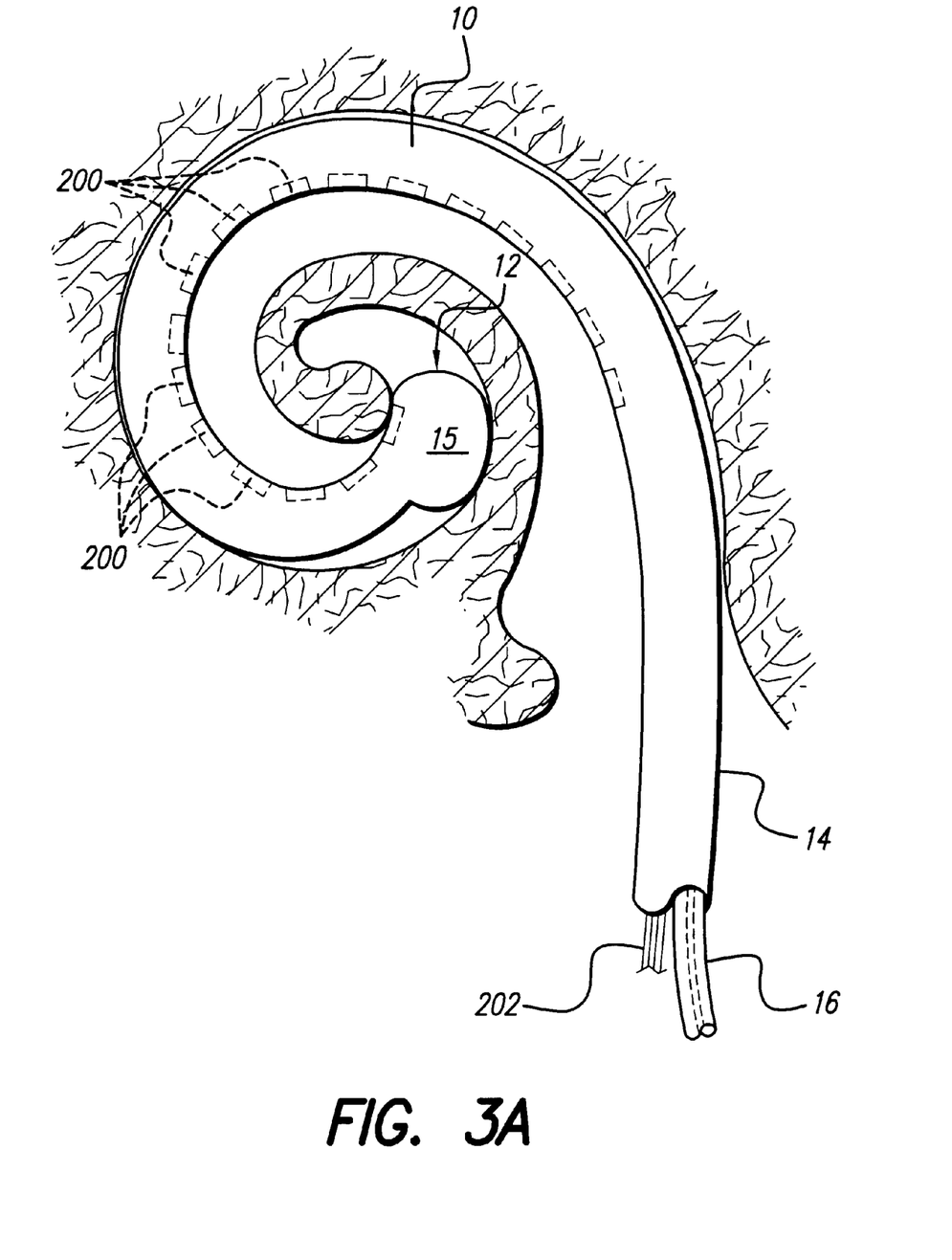
FIG. 3A illustrates a side view of the scala tympani of a human cochlea, immediately after the electrode array of FIG. 1 has been inserted therein and the inflatable compartment has been inflated.

Next, with reference to FIG. 3A, a side view of the scala tympani of a human cochlea is schematically illustrated, immediately after the electrode array 10 has been inserted therein and the inflatable compartment 15 at the distal tip of the electrode has been inflated. As seen in FIG. 3A, as a result of the inflation, the tip 12 of the electrode 10 is pushed toward the modiolar wall and wedged or anchored into the scala tympani channel, thereby positioning the electrode contacts 200 at the tip of the electrode closer to the modiolar wall and the spiral ganglion cells.

Figure 3B:
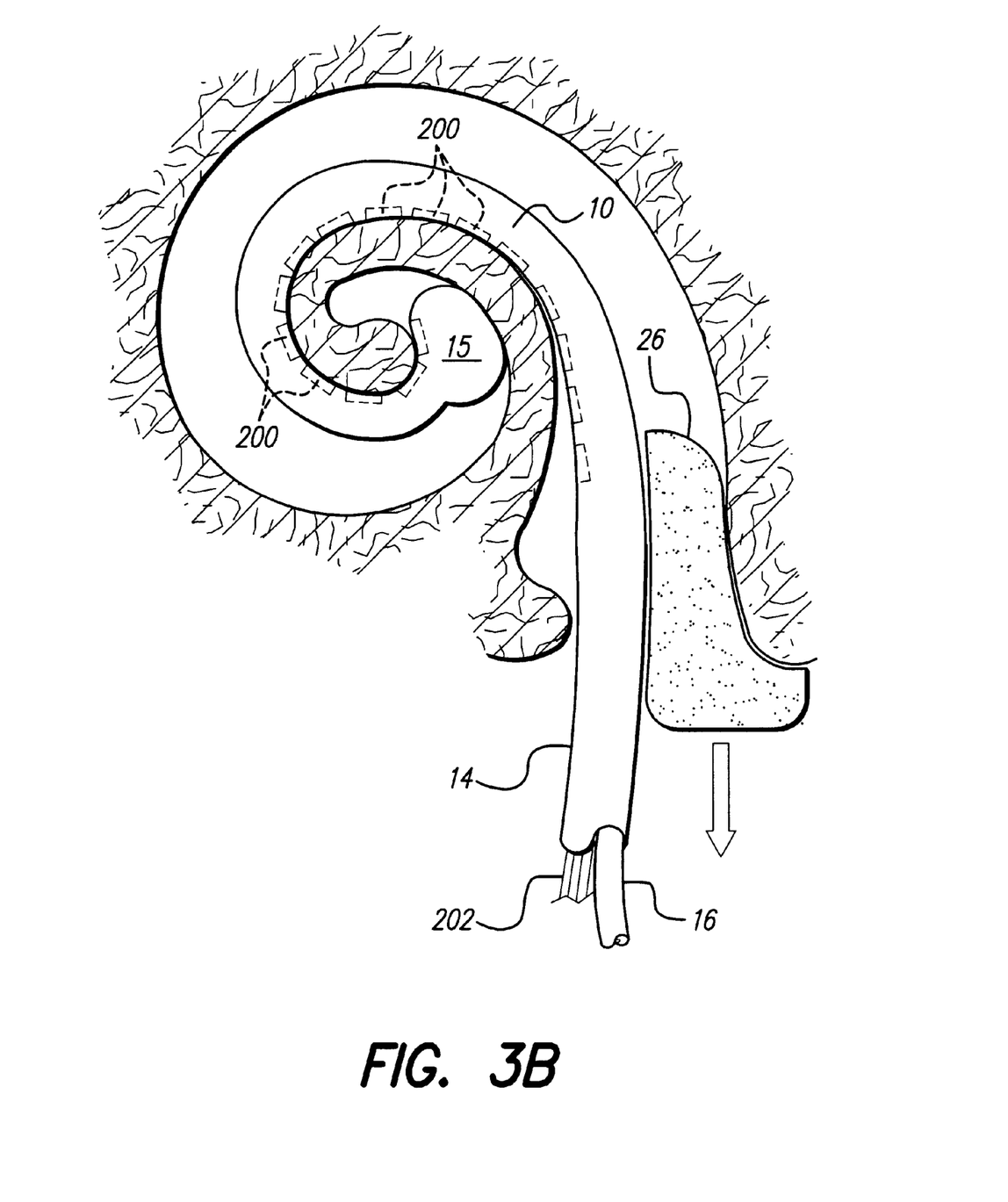
FIG. 3B is a side view as in FIG. 3A after the electrode array has been pulled back in order to snugly wrap the electrode array around the modiolus, and after a silastic plug has been inserted into the basal end of the cochlea in order to hold the electrode array in its pulled-back position where the electrode contacts reside in close proximity to the modiolar wall.

In order to position the remaining electrodes 200 (i.e., those not at the distal tip) in close proximity to the modiolar wall, the electrode 10 is pulled back (retracted out of the scala tympani) about 7 mm or so after the tip has been inflated and sealed, as illustrated in FIG. 3B. The tip of the electrode, fixed or anchored by the balloon 15, remains in place within the scala tympani while the rest of the array wraps snugly around the modiolus. Then, after pulling or retracting the electrode to the point where it is snugly wrapped or wound around the modiolus, the cochleostomy is packed with tissue or a silastic plug 26 in order to fix or anchor the electrode array 10 at the basal end. This anchoring or fixing of the electrode array at the basal end maintains the tight wrap of the electrode snugly around the modiolus. Thus, in summary, it is seen that FIG. 3B shows a side view as in FIG. 3A after the electrode array 10 has been pulled back in order to snugly wrap the electrode array 10 around the modiolus, and after a silastic or tissue plug 26 has been inserted into the basal end of the cochlea in order to hold or anchor the electrode array 10 in its pulled-back, or tight, position. Advantageously, such pulled-back, or tight position, causes the electrode contacts 200 of the array 10 to be positioned in close proximity to the modiolar wall, which is one of the primary objectives of the invention.

Figure 4:
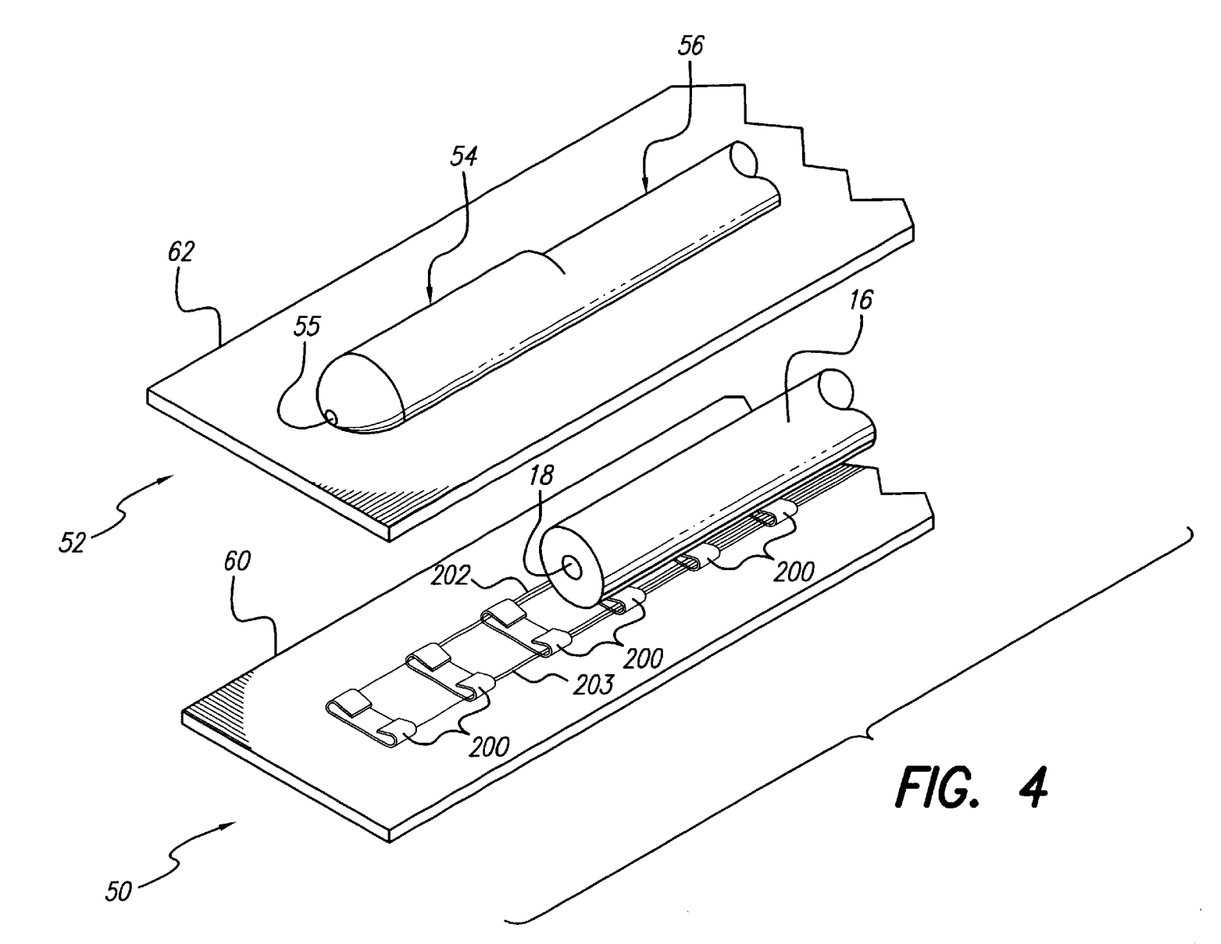
FIG. 4 depicts an exploded view of an iron-foil die used to make the first embodiment of the invention, the die including: (1) a bottom electrode contact/wire/insertion-tube assembly welded or carried on a first iron foil, and (2) a top iron foil mold made from a second iron foil.
Figure 5:
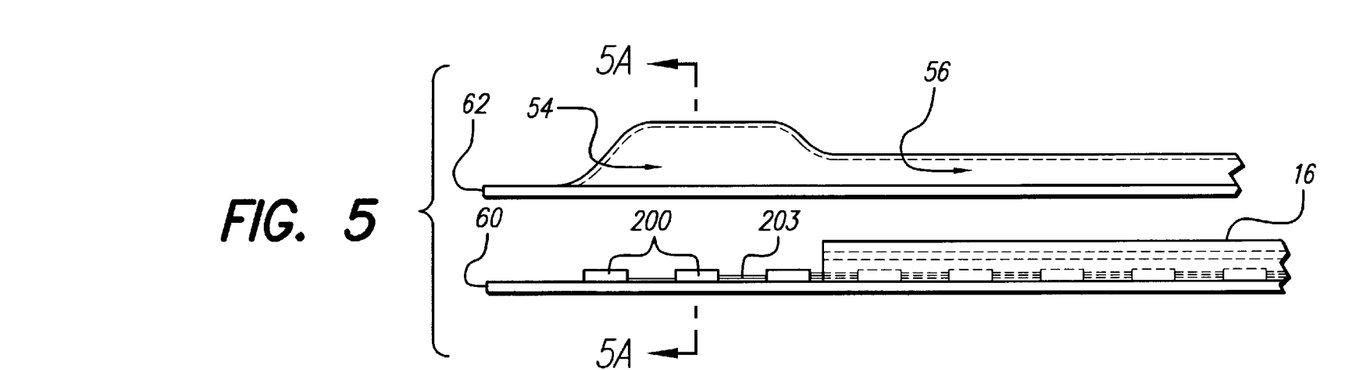
FIG. 5 shows a side view of the iron-foil die of FIG. 4 prior to sealing the side edges of the respective iron foils.
Figure 5A:
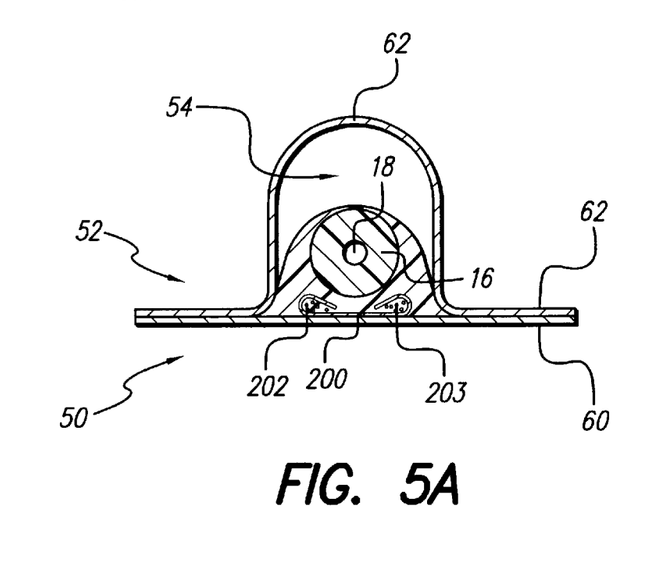
FIG. 5A is a sectional view of FIG. 5 taken along the lines 5A—5A after the side edges have been sealed.

The present invention also contemplates a method of making a cochlear electrode array 10 having an inflatable distal compartment 15. Such method is schematically illustrated in FIGS. 4, 5 and 5A. Only those details deemed necessary to understand the invention are presented herein. Other details associated with the method may be found in the referenced patent applications, and are not repeated herein.

A first step of the method involves making an electrode contact array assembly 50. The electrode contact array assembly 50, as seen in FIG. 4, includes spaced-apart electrode contacts 200, with at least one wire lead 202 or 203 attached to each electrode contact 200, and with the electrode contacts 200 being welded to a first iron foil carrier 60. This approach of using a iron foil carrier, to which the electrode contacts 200 are welded, and wherein wire bundles 202 and 203 are routed along each side of assembly 50 through an edge of the contacts 200, is more fully disclosed in the pending applications that have been previously referenced.

As a second step, the thin silicone tube 16 (which functions as the inflation tube 16 shown in FIGS. 1 through 3B, and which provides the channel 18 through which the fluid is injected into the balloon 15) is placed on top of the assembly 50 so as to reside on top of the electrode contacts 200. Typically, the edges of the electrode contacts 200 are folded over to be flat against the exposed electrode contact, as taught in the referenced applications. Alternatively, as also taught in U.S. patent application Ser. No. 09/259,199, filed Mar. 1, 1999, also incorporated herein by reference, these edges may be folded upwards, forming a U-shaped element, into which the tube 16 is placed (see, e.g., FIG. 5A of the '199 application).

Next, as a third step, and with reference to FIGS. 4, 5 and 5A, a top mold 52, pressed from a second iron foil carrier 62, is placed over the contact array/silicone tube assembly 50 (see FIG. 5) and held in place by sealing the side edges (see FIG. 5A). As seen in FIGS. 4, 5 and 5A, the top mold 52 includes an enlarged formed cavity 54 at one end of a semi-circular channel cavity 56. The cavity 54 defines the area where the thin-wall balloon 12 will be formed. The semi-circular cavity 56 defines a cavity wherein the tube 16 may reside. A vent hole 55 is made at a distal end of the cavity 54 (see FIG. 4).

The top mold 52 is placed over the assembly 50, and the edges of the top mold 52 are sealed or joined to the edges of the bottom assembly 50, thereby forming an iron die (a cross section of which is seen best in FIG. 5A). A liquid silicone elastomer is injected into the resulting iron die to fill all cavities. Soon after this is done, before the liquid silicone elastomer cures, e.g., while the silicone elastomer cures, air (or another suitable gas) is blown through the channel 18 of the inflation tube 16. This forced gas flow causes part of the silicone elastomer to be pushed out of the die cavity, and leaves a layer of silicone over the electrode contacts and wire leads of the bottom assembly 50 as well as a thin film on the inside surface of the top mold 52. This thin film on the inside surface of the top mold 52 forms the thin, expandable walls of the inflatable (balloon) section 12 of the array.

Finally, after the silicone elastomer has properly cured, chemical etching is used to etch the entire iron die away, both the bottom iron foil 60 and the top iron foil 62. This process leaves behind the electrode array 10 with a very thin-wall expandable section 12. Further details associated with the molding process, e.g., specific types of molding materials, curing times and temperatures, and the like, which details are generally known to those in the molding art, may be found in the referenced patent applications.

Figure 8A:
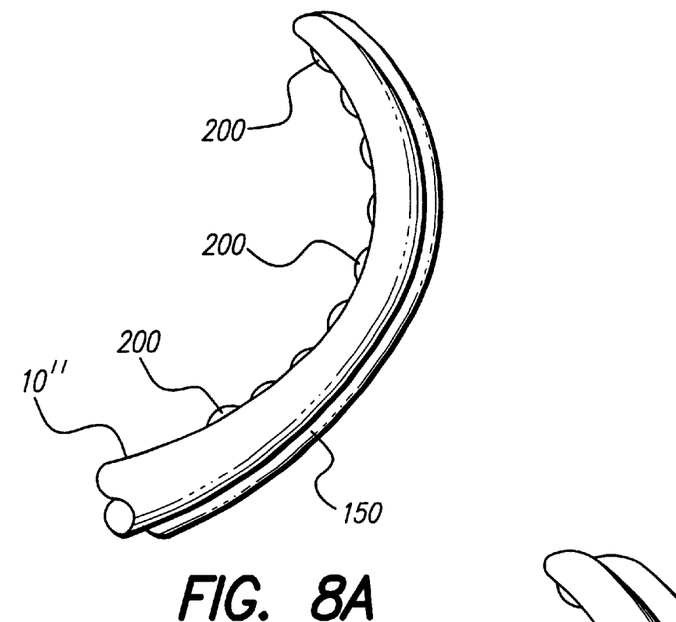
FIGS. 8A and 8B illustrate an electrode array made in accordance with the second embodiment of the invention in a deflated and inflated state, respectively.
Figure 8B:
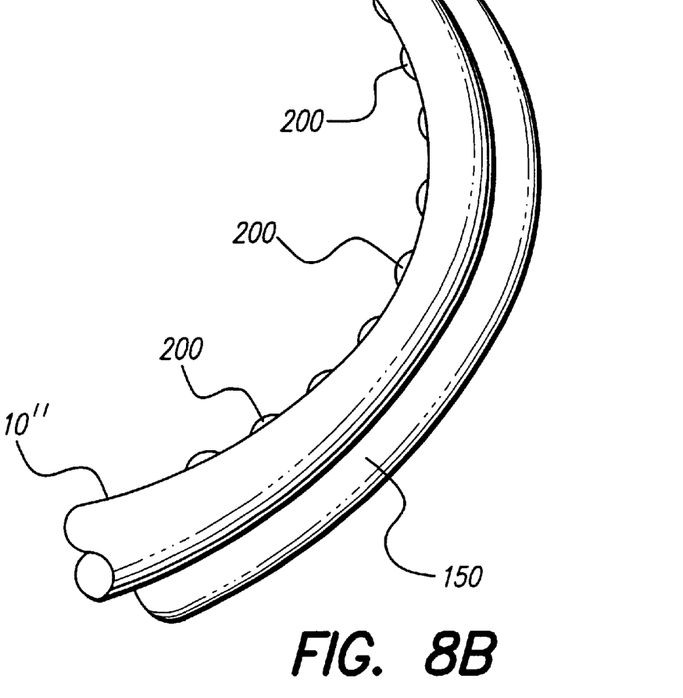

A second embodiment of the invention, similar to the first embodiment (and therefore many of the details common to both embodiments will not be repeated here), includes a thin-wall inflatable section 150 along the entire length of an electrode array 10", like a spine. This embodiment is shown in FIGS. 8A and 8B. FIG. 8A shows the inflatable spine section 150 in a deflated state; and FIG. 8B shows the spine section 150 in an inflated state. In all material aspects, the electrode array 10", with its spinal inflatable section 150, may be the same as the electrode array 10, previously described. The inflatable spine section 150 is in fluid communication with an extended injection/inflation tube 16 and associated sealing or crimping means, e.g., a crimp ring 22.

As with the first embodiment of the invention previously described, the electrode array 10" is inserted into the scala tympani in a deflated state. Once inserted to a desired depth, the inflatable spine portion is inflated by injecting a suitable fluid, e.g., saline solution, through the inflation tube 16 to file and expand the spine section. Then, the tube is sealed. This inflation causes the electrode array, with its inflatable spine portion 150, to fill the entire space of the scala tympani channel, thereby positioning the electrode contacts closer to the modiolus. As it does so, the electrode array 10" may tend to either move slightly deeper into the cochlea or to retract slightly back through the cochleostomy. However, once fully inflated, it will be locked (firmly held) in position within the cochlea, with the electrode contacts 200 positioned in close proximity to the modiolar wall, where they can more easily, i.e., with less and more focused energy, stimulate the ganglion cells.

Figure 6:
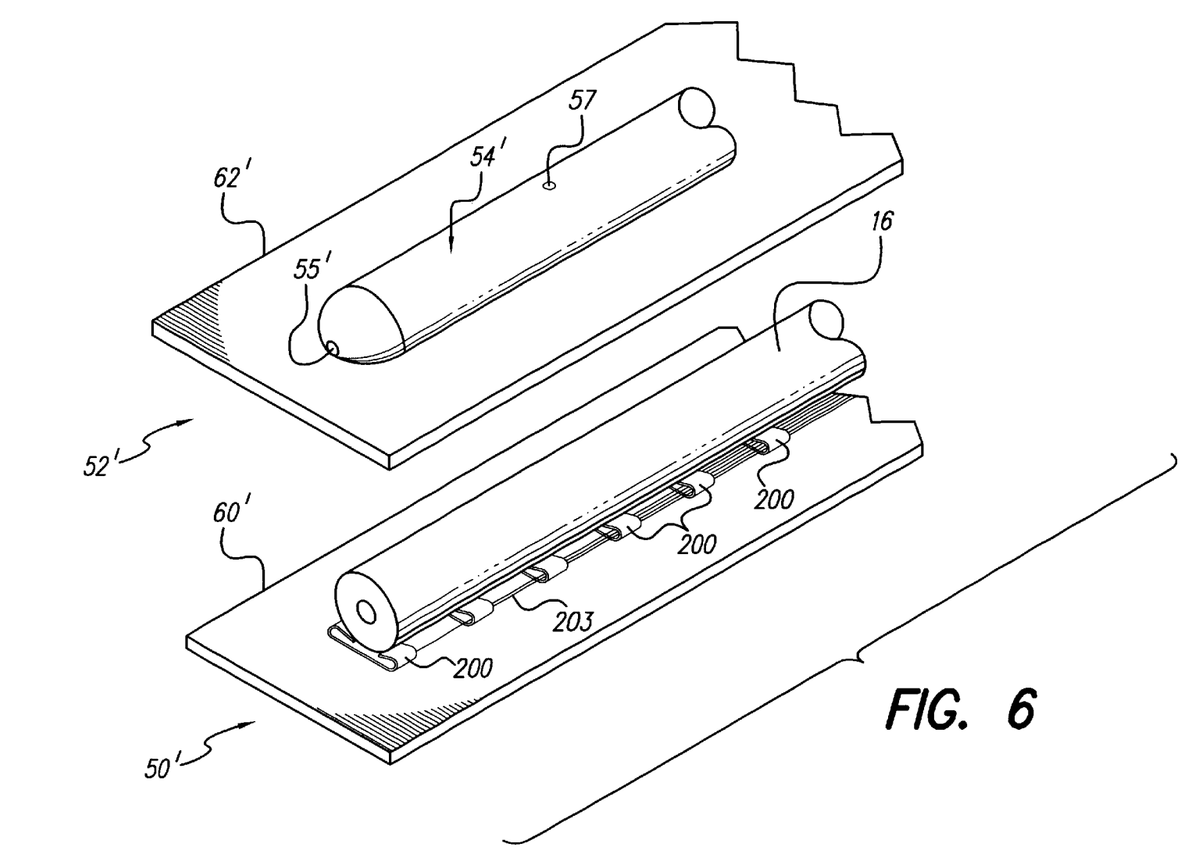
FIG. 6 depicts an exploded view of an iron-foil die, similar to the die shown in FIG. 4, that may be used to make the second embodiment of the invention.
Figure 7:
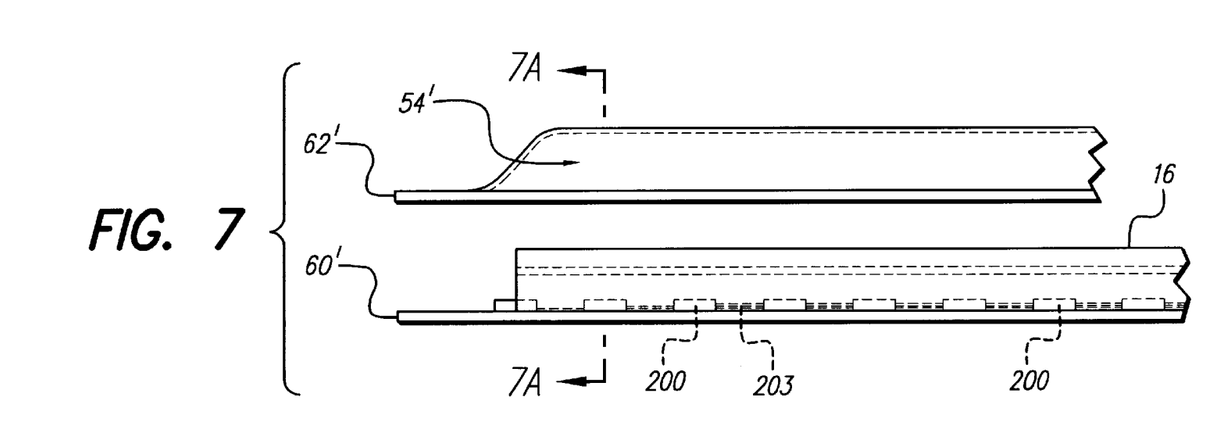
FIG. 7 shows a side view of the iron-foil die of FIG. 6 prior to sealing the side edges of the respective iron foils.
Figure 7A:
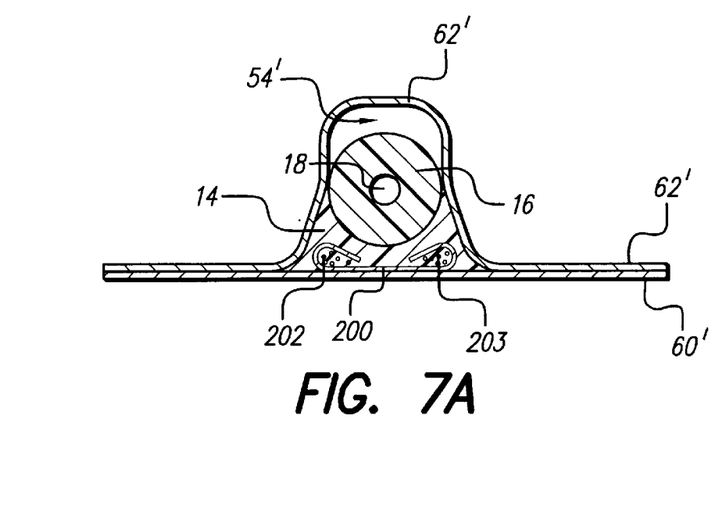
FIG. 7A is a sectional view of FIG. 7 taken along the lines 7A—7A after the side edges have been sealed.

FIGS. 6, 7 and 7A depict an iron-foil die used in connection with making the second embodiment of the invention. These figures—FIGS. 6, 7 and 7A—correspond to FIGS. 4, 5 and 5A, previously described in connection with the first embodiment of the invention, and corresponding or related reference numerals (e.g., a reference numeral with a "prime", or "'", sign thereafter) are used to identify corresponding or like parts. As can be seen from these figures, the second-embodiment die shown in FIGS. 6, 7 and 7A is essentially the same as the die shown in FIGS. 4, 5 and 5A, except that the cavity 54' in the top mold 52' extends the full length of the electrode array 10", thereby allowing the inflatable spine compartment 150 to be formed along the entire length of electrode array 10" above the injection tube 16. Note that one or more additional vent holes 57 may be used in the top mold 52' in addition to the vent hole 55', as needed, in order to assure that a film of liquid silastic forms and cures on the inside surface of the cavity 54', which thereafter becomes the thin wall of the inflatable spine portion 150.

In some variations of the second embodiment, it may be desirable to have the inflatable spine compartment 150 extend less than the full length of the electrode array, e.g., at least ½ of the length of the electrode array. In this regard, it should be noted that as the length of the inflatable distal tip portion 12 of the first embodiment increases, and as the length of the inflatable spine portion 150 of the second embodiment decreases, the two embodiments eventually merge into the same embodiment. Thus, it is seen that the present invention contemplates inflatable electrode arrays having an inflatable portion that may vary from a short distal tip portion of only about 1 mm in length up to a long spine portion that extends along the entire length of the array. (Note, a typical cochlear electrode array may be up to 25 mm long.)

As seen best in FIG. 7A (which is not necessarily drawn to scale), the area on the underneath side of the tube 16, i.e., the area between the tube 16 and the upper surface of the electrode/wire assembly 50', is filled with liquid silicone elastomer during the molding process, and cures to become, along with the body of the tube 16, the main body portion of the flexible carrier 14 of the electrode array 10". In contrast, the area above the tube 16, beneath the formed cavity 54', is the area through which the forced air (or other gas) is blown through one or more vent holes during the curing process, causing a thin wall of silastic, or silicone elastomer, to be deposited along the inside of the cavity 54'. As indicated above, when cured, this thin wall becomes the inflatable thin wall of the inflatable spine portion 150.

As with the first embodiment, once the silicone elastomer (or silastic) has cured, chemical etching is used to etch the entire iron die away, both the bottom iron foil 60' and the top iron foil 62'. This process leaves behind the electrode array 10" with a thin-wall expandable spine portion 150.

As described above, it is thus seen that the present invention provides an inflatable cochlear electrode array that helps assure that the electrode array is optimally positioned against or near the modiolar wall in a cochlea of any size. Further, it is seen that insertion of the electrode array of the present invention advantageously avoids or produces minimal trauma to the delicate cochlea during insertion because such insertion may occur while the inflatable portion of the array is deflated, or at least less than fully inflated.

Moreover, as described above it is seen that the inflatable electrode array described herein may be manufactured using easy, low cost technology and simple-to-implement manufacturing techniques.

Finally, it is seen that the inflatable electrode array of the present invention may be easily removed and reinserted into the cochlea, if required.

While the invention herein disclosed has been described by means of specific embodiments and applications thereof, numerous modifications and variations may be made thereto by those skilled in the art without departing from the scope of the invention set forth in the claims.

What is claimed is:

1. A cochlear electrode array adapted for insertion into the scala tympani of a human cochlea, one side or wall of the scala tympani comprising a modiolar wall, said electrode array comprising:

a flexible body portion;

a plurality of electrode contacts spaced apart along a first side of the body portion;

a bundle of wires embedded within the flexible body portion, at least one wire within the bundle of wires making electrical contact with at least one of the plurality of electrode contacts;

an inflatable portion extendable from a second side of the body portion opposite the first side; and a tube, having a channel passing therethrough, embedded within and integral with the flexible body portion, the channel of the tube being in fluid communication with the inflatable portion;

wherein a fluid injected through the channel into the inflatable portion causes the inflatable portion to expand; and wherein when inserted into the scala tympani with the inflatable portion deflated and with the first side of the body portion facing the modiolar wall, inflation of the inflatable portion thereafter causes the electrode array to hug the modiolar wall.

2. The cochlear electrode array of claim 1 wherein the inflatable portion comprises an inflatable distal tip portion located at a distal tip of the electrode array.

3. The cochlear electrode array of claim 2 wherein the inflatable distal tip portion has a length of between about 1 to 3 mm.

4. The cochlear electrode array of claim 1 wherein the inflatable portion comprises an inflatable spine portion that extends along the length of the cochlear electrode array.

5. The cochlear electrode array of claim 1 wherein the inflatable portion comprises an inflatable spine portion that extends along at least ½ of the length of the cochlear electrode array.

6. A inflatable cochlear electrode array adapted for insertion into the scala tympani of a human cochlea, one side or wall of the scala tympani comprising a modiolar wall, said electrode array comprising:

a flexible body portion;

a plurality of spaced-apart electrode contacts along a front edge of the body portion;

a plurality of wires embedded within the body portion, at least one wire of the plurality of wires making electrical contact with one of the plurality of electrode contacts; and an inflatable portion along a back side of the body portion, the back side being opposite the front edge of the body portion;

wherein said inflatable portion, when inflated, and when the front edge of the body portion faces the modiolar wall, causes the electrode contacts to be positioned close to the modiolar wall of the cochlea.

7. The inflatable cochlear electrode array of claim 6 wherein said inflatable portion comprises an inflatable distal tip portion at a distal tip of the electrode array.

8. The inflatable cochlear electrode array of claim 6 wherein said inflatable portion comprises a spine portion that extends along the back side at least one half of the flexible body portion.

9. The inflatable cochlear electrode array of claim 6 further including means for selectively inflating the inflatable portion with a suitable biocompatible fluid.

10. The inflatable cochlear electrode array of claim 9 wherein the means for selectively inflating the inflatable portion with a suitable biocompatible fluid comprises a tube having a channel therethrough, wherein the tube is embedded within the flexible body portion, the tube having a distal end whereat the channel is in fluid communication with the inflatable portion, the tube also having a proximal end that extends out of the flexible body portion near a proximal end of the flexible body portion, the tube having means for sealing the channel at the proximal end.

11. A method of inserting a cochlear electrode array into the cochlea, the cochlea having a modiolar wall wherein ganglion cells are located, the electrode array comprising a flexible body portion, a plurality of spaced-apart electrode contacts carried by the body portion, and a a plurality of wires embedded within the body portion, at least one wire of the plurality of wires making electrical contact with one of the plurality of electrode contacts; said method comprising the steps of:

forming an inflatable portion along a back side of the body portion;

inserting the electrode array into the cochlea to a desired depth while the inflatable portion is deflated and while the back side of the body portion faces away from the modiolar wall; and inflating the inflatable portion;

whereby the inflatable portion when inflated positions that portion of the electrode array opposite the inflatable portion against the modiolar wall.

12. The insertion method of claim 11 wherein the step of forming the inflatable portion comprises forming the inflatable portion as a spine portion that extends along the back side of the body portion a distance that is at least ½ the length of the body portion.

13. The insertion method of claim 11 wherein the step of forming the inflatable portion comprises forming the inflatable portion as a distal tip portion located at a distal tip of the body portion, and wherein when the inflatable portion is inflated only the distal tip portion of the electrode array is pushed and anchored against the modiolar wall, the method further comprising the steps of:

applying a tension force to a proximal end of the electrode array that tends to pull the electrode array rearwardly out of the cochlea, while its distal tip remains anchored in position by the inflated distal tip portion, thereby pulling the electrode array snugly against the modiolar wall; and inserting a plug into a basal end of the cochlea while maintaining the electrode array snugly against the modiolar wall, the inserted plug thereby maintaining the electrode array in its snug position against the modiolar wall.

14. A method of making an inflatable cochlear electrode comprising the steps of:

(a) making an electrode contact assembly by welding an array of electrode contacts and wire leads to a first iron foil carrier;

(b) positioning a thin silicone tube on top of the electrode contact assembly;

(c) making a top mold assembly with at least one vent hole therein by press-forming a balloon cavity in a second iron foil carrier;

(d) making an iron die of the cochlear electrode by placing the top mold assembly over the electrode contact assembly and sealing the side edges of the first iron foil to the second iron foil;

(e) filling all cavities within the iron die with a liquid silicone elastomer;

(f) blowing a gas through the silicone tube as the liquid silicone elastomer cures, thereby causing a layer of silicone elastomer to form over the electrode contact assembly, including the electrode contacts, wire leads and silicone tube, and causing a thin film of silicone elastomer to form on a inside surface of the balloon cavity of the top mold assembly; and (g) chemically etching away the first and second iron foils, thereby leaving an electrode array having a thin-wall expandable section in fluid communication with the silicone tube, which silicone tube is embedded within the electrode array along with the wire leads and all but an exposed surface of each electrode contact of the electrode contact assembly.

15. An inflatable cochlear electrode array adapted for insertion into a human cochlea having a modiolar wall comprising:

a flexible body portion having a medial side adapted to face the modiolar wall when inserted into the cochlea;

an inflatable spine portion integral with the flexible body portion and opposite the medial side;

wherein the flexible body portion has a multiplicity of spaced-apart electrode contacts and respective wires that make electrical contact with each electrode contact, and wherein the electrode contacts are urged closer to the modiolar wall when the inflatable spine portion is inflated.

16. The inflatable cochlear electrode array of claim 15 wherein the inflatable spine portion extends at least ½ of the length of the flexible body portion of the electrode array.

* * * * *